United States Patent [19]
Jones et al.

[11] Patent Number: 5,744,096
[45] Date of Patent: Apr. 28, 1998

[54] AUTOMATED IMMUNOASSAY CASSETTE

[75] Inventors: Ronald M. Jones, Mountain View; Eric G. Barr, Fremont; Gary E. Hewett, San Leandro, all of Calif.

[73] Assignee: Cholestech Corporation, Hayward, Calif.

[21] Appl. No.: 803,677

[22] Filed: Feb. 21, 1997

[51] Int. Cl.$^6$ .................................................. G01N 35/10
[52] U.S. Cl. ........................... 422/58; 422/63; 422/66; 422/100; 436/43; 436/44; 436/164; 436/165; 436/180; 436/805; 436/807; 436/518
[58] Field of Search ........................ 422/58, 63, 66, 422/100, 103, 104; 436/43, 44, 164, 165, 169, 170, 174, 180, 805, 807, 518

[56] References Cited

U.S. PATENT DOCUMENTS

| | | |
|---|---|---|
| 4,826,759 | 5/1989 | Guire et al. . |
| 4,839,297 | 6/1989 | Freitag et al. . |
| 4,959,324 | 9/1990 | Ramel et al. . |
| 4,999,287 | 3/1991 | Allen et al. . |
| 5,260,221 | 11/1993 | Ramel et al. . |
| 5,260,222 | 11/1993 | Patel et al. . |
| 5,416,000 | 5/1995 | Allen et al. . |
| 5,468,647 | 11/1995 | Skold et al. . |

FOREIGN PATENT DOCUMENTS

WO 93/13856  7/1993  WIPO .

*Primary Examiner*—Long V. Le
*Attorney, Agent, or Firm*—LeeAnn Gorthey

[57] ABSTRACT

The invention relates to an immunoassay cassette useful for carrying out multistage immunoassays in an automated manner. In operation, the cassette assumes different operational positions in which solutions are transferred sequentially across an absorbent pathway containing assay reagents.

12 Claims, 3 Drawing Sheets

Fig. 4

AUTOMATED IMMUNOASSAY CASSETTE

FIELD OF THE INVENTION

The present invention is directed to a device for use in assaying a body fluid sample for a selected analyte, and particularly for use in automated multistage assays.

References

Black, D. et al., Anal. Biochem. 169:197–203 (1988).
Black, D. et al., Annals of Rheumatic Diseases 48:641–644 (1989).
Cerelli, M. J. et al., PCT Pubn. No. 94/03814 (1994).
Cook, J. et al., Ann. Clin. Biochem. 12:219 (1975).
Harlow, E. et al., "Antibodies: A Laboratory Manual", Cold Spring Harbor Lab (1988).
Hewett, G. E., U.S. Pat. No. 5,110,724 (1992).
Hewett, G. E. et al., U.S. Pat. No. 5,171,688 (1992).
Leuvering et al., U.S. Pat. No. 4,313,734 (1982).
Macek, J. et al., Z. Rheumatol. 46:237–240 (1987).
Robins, S. P., in "Collagen in Health and Disease" (Weiss, J. B. et al., eds.) pp. 160–178, Churchill Livingstone, Edinburgh (1982).
Siebel et al., J. Rheumatol. 16:964–970 (1989).

BACKGROUND OF THE INVENTION

Assays for detecting the presence and level of a variety of analytes in body fluid samples are known. Such assays are often designed for simplicity of use so that they can be reliably conducted in a doctor's office or other clinical setting where personnel may have little training in clinical assay procedure or in interpreting assay results. In order to minimize the need for operator involvement, it is preferable that the assay be carried out in an automated or self-contained manner.

Such self-contained assays have typically been limited, for the sake of simplicity of operation, to one-step assay procedures. A number of useful assays, however, are multistage in nature, requiring more than one reacting or binding step, or requiring a separate washing step to remove unbound materials from a substrate. Because of the need for additional operations such as adding or removing solutions, or moving a test strip from one solution to another, multistage assays are less readily automated and generally require more input from the user, thus increasing the possibility of error.

It is therefore desirable to provide an automated, self-contained assay device which is able to perform multistage assays, in particular those containing a reacting or binding step followed by a washing step, with minimal operator input.

Another problem frequently encountered in flowthrough type assays carried out on absorbent strips is uneven development, in the region designated for detection, of the detectable species. It is therefore also desirable to provide features within an assay strip which increase the uniformity of distribution of detectable species that develop on the strip.

SUMMARY OF THE INVENTION

The invention provides, in one aspect, an immunoassay cassette for use in detecting an analyte in a body-fluid sample. The cassette includes a base, a reagent support, and means for mounting the support on the base, allowing relative movement of these two components from an initial at-rest position, to assume first and second operational positions. The mounting means are preferably compressible supports on the base, effective to support opposite ends of the reagent support.

Included on the base are: a sample well for containing sample, a sample-transfer strip for transferring sample from the sample well to a sample-transfer position, a wash reservoir for containing a wash solution, a wash-transfer strip for transferring wash from the wash reservoir to a wash-transfer position, and a takeup pad for imbibing wash solution.

Included on the reagent support are a reaction strip and an analyte detection zone. The reaction strip is composed of capillary means capable of transferring fluid. In particular, the reaction strip is effective to transfer sample fluid from the sample-transfer position to the detection zone, when the reagent support is moved to its first operational position, and to transfer wash solution from the wash-transfer position to the detection zone, when the reagent support is moved to its second operational position. The takeup pad, above, is effective to imbibe liquid from the detection zone when the reagent support is moved to its second operational position.

The cassette further includes assay reagents disposed in the fluid pathway defined by the sample-transfer strip, reaction strip, and detection zone. These reagents, also referred to as reagent means, are effective to produce a detectable, analyte-dependent reaction product at the detection zone.

The relative movement of the reagent support and base between said first and second operational positions is effective to break contact between the simple-transfer position and the reaction strip, and to establish contact between the wash-transfer position and said reaction strip. In one embodiment, the simple-transfer strip has an overhang region, containing the sample transfer position, which is adapted to contact the reaction strip in the first operational position, and to shift to a position of non-contact with the reaction strip in the second operational position.

In a preferred embodiment, the reagent support further includes a control reaction zone. In this case, the mounting means permits relative movement between the support and the base to assume a third, or control, operational position, where contact is established between the sample transfer strip and the control reaction zone.

The reagent means may include a labelled ligand effective to bind selectively with the sample analyte, where the reaction product is a detectable analyte-ligand complex formed by such binding. Alternatively, the reagent means may include (i) a labelled ligand effective to bind selectively with the sample analyte and (ii) a substance effective to competitively bind with the labelled ligand, in which case the reaction product is a detectable substance-ligand complex formed by such competitive binding. In one embodiment, the body fluid sample is a urine sample, and the analyte is pyridinoline or deoxypyridinoline.

In a preferred embodiment, the cassette further includes a strip of uniform polymeric mesh disposed between and adjoining the reaction strip and the detection zone. In another preferred embodiment, the reagent means is applied to the detection zone in a reverse concentration gradient, such that the concentration increases in a downstream direction across the detection zone.

In another aspect, the invention provides an assay apparatus for detecting an analyte in a body fluid sample. This apparatus includes an immunoassay cassette as described above and a cassette reader. The cassette reader includes an aperture for receiving the cassette therein, and means for moving the reagent support of the cassette relative to the base from its at-rest position, to its first, second and third operational conditions, at predetermined times. The apparatus preferably further includes means for detecting the assay reaction product.

DETAILED DESCRIPTION OF THE INVENTION

I. Immunoassay Cassette

Figure 1:
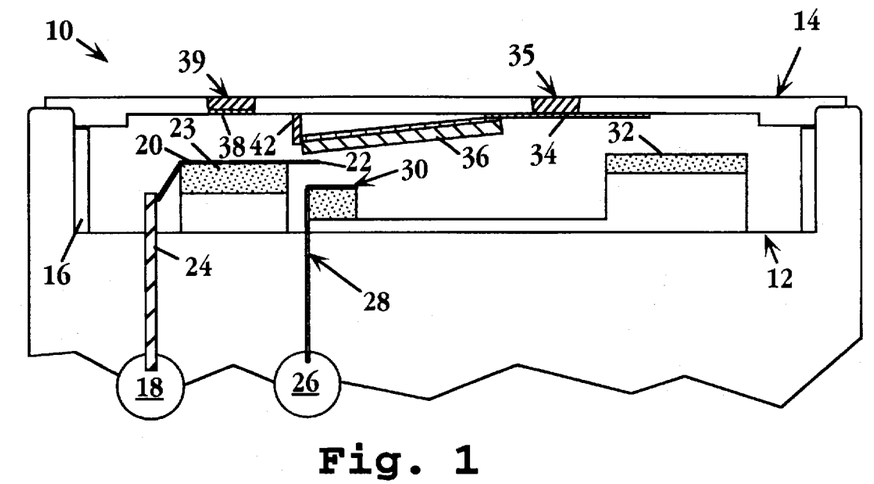
FIG. 1 shows an immunoassay cassette constructed in accordance with one embodiment of the invention, with the cassette in an initial at-rest or sample loading position.

FIG. 1 shows an immunoassay cassette 10 constructed according to one embodiment of the invention. The cassette contains two plate-like members, a base member 12 and a reagent support member 14, which may be produced by standard molding or machining methods. The reagent support is mounted on the base via adjustable side members 16, also defined herein as mounting means. The mounting means allows the relative positions of the base and reagent support to be adjusted from an initial at-rest position to assume different operational positions, as described below.

Figure 2:
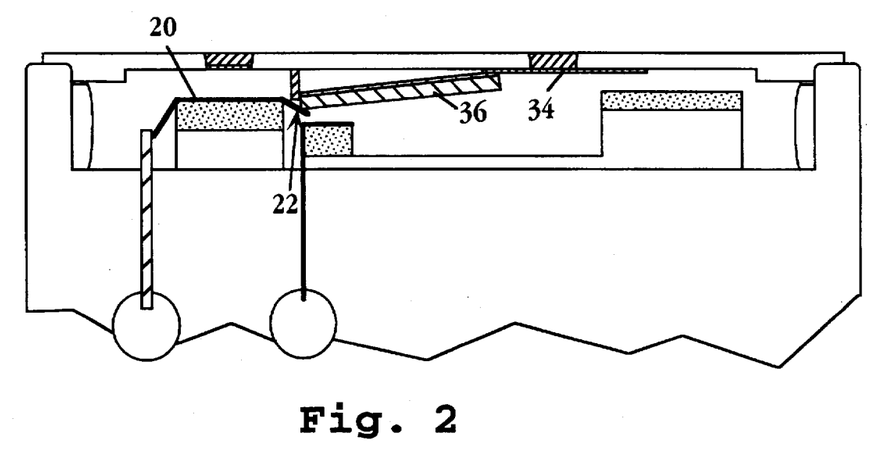
FIG. 2 shows the cassette in a first operational (reacting) position.
Figure 3A:
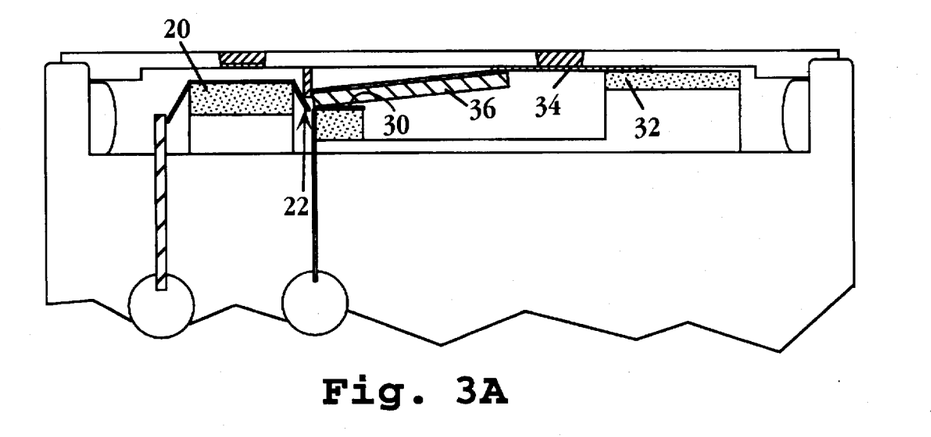
FIG. 3A shows the cassette in a second operational (washing) position.
Figure 3B:
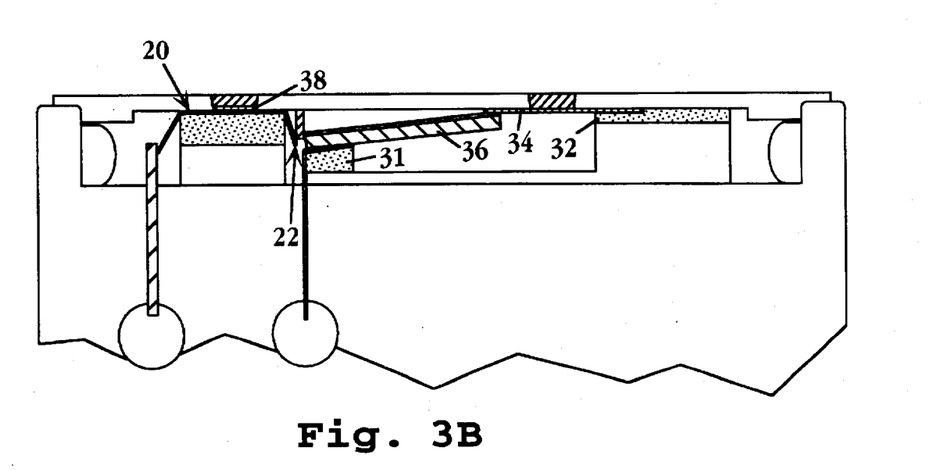
FIG. 3B shows the cassette in a third operational position which further incorporates a control reaction.

The mounting means may be compressible blocks, as shown at 16, which support opposite ends of the reagent support. These blocks become further compressed as the cassette assumes successive operational positions, as illustrated in FIGS. 1–3. The support blocks could also be compressed by means of springs or a piston-like action.

In operation, the cassette is preferably contained within a cassette reader. The reagent support member contacts a supporting surface within the reader, and mechanical means within the reader engage the base member and are effective to move it incrementally toward the reagent support. Alternatively, the base could be held stationary and the reagent support moved incrementally. The mechanical means within the cassette reader may include conventional components such as clamps, pistons, stepper motors, worm gears, or the like. It will also be appreciated that the base and reagent support members could be separately engaged and shifted within the reader without the use of supports as shown as 16, in which case the mechanical means within the reader would comprise the mounting means.

Provided within base 12 is a sample well 18 for containing the body fluid sample to be analyzed. Adjacent the sample well, so that they may be brought into fluid communication, is a sample transfer strip 20. When strip 20 is placed in fluid communication with the sample, the strip is effective to transfer the sample, by capillary action, to sample transfer position 22. This position is defined as the portion of sample transfer strip 20 which, during operation, comes into contact with the reaction strip of the cassette, as described below.

The sample transfer strip is made of a strip of bibulous, fibrous material capable of drawing fluid via capillary flow. A variety of fibrous materials, such as are commonly used in fibrous-mat filters, including cellulose, cellulose acetate, and glass fibrous matrices, are suitable materials for the transfer strip. The fibers may be crosslinked, if desired, by chemical crosslinking, heat fusion, or the like. Also suitable are porous substrates, such as sintered glass, fused polymer beads, and the like, whose wettability and dimension of interstices are such as to promote movement of an aqueous medium into the strip by surface wetting. One exemplary material is a glass fiber filter having a packing density of about 0.2–0.5 gm/cm$^3$.

The strip may be mounted on a backing made of plastic or other inert supportive material. The backing material is preferably flexible. The overhang portion of the strip, as shown in FIGS. 1–3, must be capable of flexing from its at-rest position, as discussed further below. The strip and backing are supported on sample block 23, which may be composed of a compressible material such as foamed rubber.

A wick may also be provided between the sample well and the sample transfer strip, such as shown at 24 in FIG. 1. The wick is typically of a lower density material than the sample transfer strip, to allow for more rapid transfer of sample. One suitable material is a pad of high molecular weight polyethylene fibers, such as may also be used for the reaction strip, described below.

A filter (not shown) may be incorporated into the sample well or wick to remove particulates and interfering substances from the sample prior to the assay. Selection of appropriate filter materials is described, for example, in PCT Pubn. No. WO 94/03814, by Cerelli.

Also provided within base 12 is a wash reservoir 26 to contain wash solution. Wash transfer strip 28, also made of a bibulous material, is provided for transferring the wash solution from reservoir 26 to a wash transfer position 30. This position is defined as the portion of wash transfer strip 28 which comes into contact, during operation, with the reaction strip of the cassette, as described below. Wash transfer strip 30 is typically mounted on an inert backing material, similar to that used for sample transfer strip 20, and supported on support block 31, as shown, which is preferably composed of a compressible material, such as foam rubber.

The base member also contains a fluid takeup station which includes absorbent wash takeup pad 32. The pad is able to imbibe liquid from the detection zone of the cassette when placed in contact with same, as described below. The absorbent pad is preferably formed of a compressible material, or it may be mounted on a compressible support block.

The reagent support member contains an analyte detection zone 34, made of an absorbent material through which fluid may flow by capillary action and on which reagent means, described below, may be immobilized. Preferred materials include porous, fused polymer or microporous polymer membranes, such as polysulfone, polypropylene, nylon, nitrocellulose, Teflon™, or polyvinylchloride microporous membranes. In the present case, nitrocellulose, such as is available from Millipore, cast onto a sheet of clear Mylar™ or similar material, is particularly preferred. One or more windows, such as that shown at 35, are preferably provided within reagent support member 14 to allow convenient detection of optically detectable reaction products formed within the detection zone.

Adjacent the detection zone is a reaction strip 36, also referred to herein as capillary means. The reaction strip is also made of an absorbent material, such as those described above, able to transport fluid by capillary action. This is preferably a filter of high molecular weight polyethylene fibers, such as provided by Porex. Suitable materials include Porex 4588, which has a thickness of 0.028" (approx. 700 µm) and an average pore size of 70 µm, and Porex T3, which has a thickness of 0.022Δ (approx. 550 µm) and an average pore size of 7 µm. The reaction strip is also mounted on a solid inert backing, as shown at 37 in FIG. 4.

The filter, sample transfer strip and detection zone are typically each about 1–5 cm, preferably 1–2 cm, in length, and 1–10 mm in width, with the three components having approximately the same width. The transfer strip and detection zone are typically about 100–150µ in thickness. The filter making up the reaction strip is generally thicker, as described above, having a thickness of about 150–1000 µm, and preferably about 500–750 µm.

Any of the regions described, including the sample transfer strip, reaction strip and detection zone, may be dimensioned to absorb a defined volume of sample fluid, typically about 3–25 µl, and preferably between about 15–25 µl, thus permitting control of sample volume. In a typical assay, as described below, the reaction strip absorbs a 20 µl aliquot of sample.

Disposed within the fluid pathway defined by the sample transfer strip, the reaction strip and the detection zone are reagents, described further below, effective to produce a detectable, analyte-dependent reaction product which is detected at the detection zone. Various assays may therefore be carried out using the cassette, as described below.

In the embodiment shown, the reagent support also contains a control reaction zone 38. The control zone contains a wettable, absorbent test pad or membrane which contains reagents effective to carry out a control reaction with a portion of the body fluid sample. A window, as shown at 39, is preferably provided to allow convenient detection of optically detectable reaction products formed within the control zone.

Figure 4:
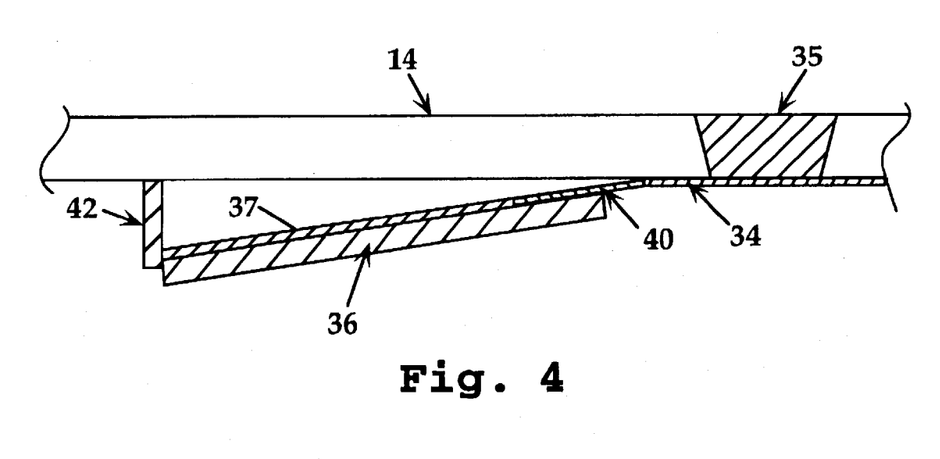
FIG. 4 shows a detail view of a section of the reaction support member of the cassette, in one embodiment of the invention, showing the reaction strip and detection zone.

In a preferred embodiment, a narrow strip of polymeric mesh, as shown at 40 in FIG. 4, is disposed between and adjoining reaction strip 36 and detection zone 34. The strip is essentially the same width as the reaction strip and detection zone, but, as shown, is significantly shorter than these components, e.g. about 0.5 to 5 mm, preferably 1–3 mm, in length. The mesh material is more uniform in composition than the material, typically glass fibers, used for the reaction strip, such that any non-homogenous solution entering the mesh from the reaction strip becomes more uniformly mixed within the mesh. One suitable material is a polyester mesh, e.g. Tetko 7-7/1, available from Tetko Inc., Briarcliff Manor, N.Y. Inclusion of this strip thereby reduces streaking of the sample fluid, with any dissolved reagents, as it enters the detection zone, and provides more uniform development of detectable species in the detection zone.

In another preferred embodiment, the reagents or species within the detection zone are applied in a reverse gradient; that is, with the lowest concentration of reagent on the leading edge of the detection zone, such that concentration increases in a downstream direction. This modification reduces overdevelopment at the leading edge of the zone, where incoming sample first makes contact, resulting in more uniform development of detectable species. Such a gradient may be produced by applying reagent using an ink-jet sprayer adapted for biological fluids. Such sprayers are available from Ivek Corporation, North Springfield, Vt. and by Synergy Research, West Lebanon, N.H. A preferred sprayer from Synergy Research, the PicoJet™ 810, is able to dispense precise numbers of microdroplets onto various substrate materials and provides precise control of droplet count and placement.

As noted above, the cassette is preferably contained during operation within a cassette reader, which includes an aperture for receiving the cassette and means for adjusting the relative positions of the base and reagent support, e.g. by means of internal components which separately engage these elements. As described above, in a preferred design, the reagent support member of the cassette engages a support surface when the cassette is inserted into the reader, and the base member is incrementally moved toward the reagent support. Such adjustments are made at predetermined times during operation to assume the operational positions described below.

The cassette reader preferably incorporates means for detecting assay reaction products within the detection zone of the cassette. Optical access to the detection zone is provided through window(s) 35 and/or 39. For this purpose, optical alignment pins (not shown) may be included on the upper surface of the reagent support, for engaging by the surface within the reader which contacts the reagent support.

When reflectance spectroscopy, a preferred method, is used for detection, the detector includes a light source and a reflected light detector. The source, which directs a focused selected-wavelength light beam at the measurement position, may be a low-power laser, a monochromatic, noncoherent light source whose beam is focused by a suitable lens arrangement, an LED, or the like. The detector is typically a conventional light sensor, such as a photovoltaic sensor, which outputs a light intensity signal value. The signal values from the detector are supplied to a digital processor which converts percent reflectance to level of analyte by comparison to reflectance of standard samples, according to procedures known in the art.

II. Operational Positions of the Cassette

As noted above, the base and reagent support members are able to sequentially assume different relative positions, including an at-rest position and first and second operational positions. According to an important feature of the invention, selected components move into and out of contact with one another as the different operational positions are assumed, as described below.

In the at-rest position, shown in FIG. 1, no contact occurs among sample transfer strip 20 (which includes sample transfer position 22), reaction strip 36, and detection zone 34. This position is also a sample loading position, in that sample flow through the sample transfer strip is initiated when the strip, or wick 24 when present, is placed in contact with sample fluid in the sample well.

In the first operational position, shown in FIG. 2, contact is established between the sample transfer strip, at sample transfer position 22, and reaction strip 36, enabling sample fluid to be transported from the sample transfer strip to the reaction strip, and thereby to detection zone 34. This position is also referred to as a reacting position.

When the cassette shifts from the first to the second operational position, as shown in FIGS. 3A–3B, the contact between sample transfer position 22 and reaction strip 36 is discontinued, and contact is established between wash transfer position 30 and the reaction strip. Accordingly, wash fluid from wash reservoir 26 is transported via wash transfer strip 28 and wash transfer position 30 to the reaction strip, and thereby to detection zone 34. In addition, as can be seen from FIG. 3A, contact between the detection zone and pad 32, which thereby acts as a wash fluid takeup station, is established in this operational position.

FIG. 3B illustrates a third operational position, in which control zone 38 makes contact with sample transfer strip 20, thus initiating a control reaction. In the embodiment shown, support block 31 and pad 32 assume a compressed position in order for such contact to be made, but flow of wash solution from the wash reservoir to wash takeup pad 32 is unaffected. Thus, reaction at control zone 38 may occur concurrently with the assay itself, rather than subsequently. Because only brief contact between the control zone and sample transfer strip is generally required for transfer of sample, the cassette typically remains in the position shown in FIG. 3B for only a brief period, and then may be shifted to the position shown in FIG. 3A.

Upon moving from the first to the second operational position, the cassette effectively shifts from a reacting phase, in which sample is transported to regions of the reagent support and undergoes an analyte-dependent reaction, to a washing phase, in which unbound reagents or other species are removed from the reaction strip and detection zone. Such steps are included in various assays and can be carried out, using the present cassette, in an automated and efficient manner.

Although the second operational position is generally referred to as a washing position, and the solution transported therein as a wash solution, it should also be appreciated that the second operational position of the cassette, as shown in FIG. 3A or 3B, could incorporate a further reagent solution rather than a wash solution, thus providing a second reacting phase rather than a washing phase.

Of the various designs that could be employed for breaking contact between sample transfer position 20 and reaction strip 36, a preferred design is shown in FIGS. 3A-3B. Here, a nonabsorbent barrier 42 is situated adjacent the reaction strip in the vicinity of its point of contact with the sample transfer position. The overhang portion of the sample transfer strip containing transfer position 20 is flexible, as noted above. In the first operational position, this portion contacts the reaction strip, as shown in FIG. 2. In the second and third operational positions, shown in FIGS. 3A-3B, it shifts to a non-contact position with the reaction strip, i.e. by impinging against barrier 42. As shown, the barrier bridges, or may fill, a gap between the reaction strip and reagent support 14. Alternatively, barrier 42 is absent, and, in the second operational position, sample transfer position 20 is able to bypass reaction strip 36 and reside in this gap.

As can be seen from FIGS. 3A-3B, breaking contact between the sample transfer strip and the reaction strip is concurrent with the establishing of contact between wash transfer strip 28 and the reaction strip. Thus, according to an advantage provided by the invention, the immunoassay cassette switches from a first, reacting phase of an assay to a second phase, such as a washing phase, in an automated, self-contained manner, without the necessity of addition of solutions or other operator input. Other means of breaking contact could also be envisioned; e.g. by lateral movement (that is, perpendicular to the plane of the Figures) between the sample transfer strip and wash strip, which in this case would be laterally offset.

III. Assays and Assay Reagents

A. Types of Assays

The immunoassay cassette is suitable for automated and self-contained execution of various immunochemical assays. For this purpose, immunochemical reagents, also referred to herein as reagent means, are contained in the fluid path defined by sample transfer strip 20, reaction strip 36, and detection zone 34.

In an example of a competitive-binding type assay, the detection zone is impregnated with an analog of the analyte species in immobilized form. The fluid sample containing analyte is contacted with a known quantity of a labelled ligand, which binds selectively to the analyte to form an analyte-antibody complex. This ligand may be loaded onto the sample transfer strip, or, preferably, onto the reaction strip, in soluble form, such that the sample fluid traversing the given region dissolves the ligand, which binds to the analyte within the sample fluid. The resulting solution, upon reaching the detection zone, contains unbound antibody in inverse relation to the quantity of analyte in the sample. This unbound labelled antibody then binds to the analog immobilized within the detection zone.

The above steps take place while the cassette of the invention is in its first operational position, or reaction phase. After a suitable incubation period, if necessary, the base and reagent support within the cassette are shifted to the second operational position, such that a fluid path is established between the wash reservoir, reaction strip, detection zone, and wash intake station, e.g. as shown in FIG. 2. Wash fluid is thereby able to traverse the reaction strip and detection zone and remove unbound species, which include, in this case, remaining unbound antibody and analyte-antibody complex. Immobilized analog-antibody complex remains in the detection zone, in a quantity that is inversely related to the amount of analyte in the body fluid sample. This complex is then detected via conventional methods, depending on the type of labelling used for the detectable species.

Many methods of labelling a secondary ligand are known in the art, including the use of radiolabels, fluorescent labels, or linked enzymes which convert a separate substrate to a detectable species. A variety of reporter-labelled antibodies, such as enzyme-labelled antibodies, are commercially available or may be readily prepared according to known methods (see, e.g., Harlow, pp. 319-358).

For the immunoassay cassette of the present invention, optically detectable labelling methods are preferred. Enzymes which react with a substrate to produce a visible reaction product are widely used for this purpose. One preferred enzyme is alkaline phosphatase, which reacts with a p-nitrophenylphosphate substrate to produce a colored product having a strong absorption peak at 405 nm.

A particularly preferred labelled ligand is an analyte-specific antibody conjugated to a visible particle such as a colored latex bead or colloidal gold. Such conjugates are described in U.S. Pat. No. 4,313,734 (Leuvering) and may also be obtained from manufacturers such as BB International (Cardiff, UK) and NanoProbes (Stony Brook, N.Y.).

A specific example of the above-described competitive-binding assay is described below in Section B. It will be appreciated one of skill in the art could use the described cassette to perform a variety of different assays, using different assay reagents, without departing from the spirit of the invention.

For example, the sample transfer strip may contain soluble antibody effective to bind with a sample analyte, while the reaction strip contains binding reagents effective to immobilize unbound antibody, thus allowing only the soluble analyte-antibody complex to diffuse to the detection zone. The antibody may be detected therein via an attached label, as described above. Alternatively, the detection zone may contain reagents effective to produce a detectable reaction product with unlabeled antibody-analyte complex. For example, the detection zone may contain an oxidase, a peroxidase, and a compound oxidizable to a detectable species such as a dye. When the analyte-antibody complex includes a substrate for the oxidase, the $H_2O_2$ generated in the resulting reaction reacts with the oxidizable compound, catalyzed by the peroxidase, to generate the detectable dye. Such assays are described, for example, in Hewett et al.

The cassette is also suitable for performing sandwich-type assays, where a molecule simultaneously binds a "capture" moiety and a "detector" moiety. These include conventional assays in which analyte is selectively bound to a substrate containing immobilized ligand, unbound sample components are removed by washing, a detectable selectively-binding ligand is added, and unbound ligand is washed away. In one variation, the ligand which selectively binds the analyte species is immobilized within the detection zone, and the analyte is detected by selective binding to a detectable secondary ligand present in the fluid pathway defined above, e.g. within the sample transfer strip or reaction strip.

From the above description, it will be clear how the various objects and advantages of the invention are met. The described cassette may be used to perform a variety of multistage assays, including different reagents within the various zones and reservoirs of the cassette, in an automated fashion, with little or no outside input during operation. The cassette is particularly useful for performing assays which include sequential steps in which reagent and/or wash solutions are transported across a fixed support. When required, multiple reservoirs, and/or multiple reacting/washing sequences, could be used.

An important feature of the invention, as described above, is automated movement between operational positions, described herein as reacting and washing positions, effective to sequentially transfer different solutions across the fixed surfaces in a single-flow-path configuration.

Preferably, the cassette is supplied with solutions and reagents preloaded and is thus entirely self-contained, not requiring operator loading of solutions. The reader containing the cassette may be programmed to adjust the cassette to its different operational positions at designated times. A multiple-stage assay may thus be carried out with the cassette contained within a cassette reader, requiring no outside operator input.

B. Representative Assay: Determination of Pyridinium Crosslink Levels in Urine

In a specific application of the present device, a urine sample is analyzed for levels of pyridinoline (Pyd) or deoxypyridinoline (Dpd). Altered levels of these compounds, which are members of a class of compounds found in urine known as pyridinium crosslinks, have been shown to be diagnostic of disorders characterized by an abnormal balance between bone formation and bone resorption, such as osteoporosis (Robins, Macek, Black). Creatinine level is measured as a control to normalize analyte levels to urine concentration and skeletal mass.

Sample is prepared by diluting in an appropriate medium, e.g. approximately three volumes of buffer (PBS, phosphate buffered saline) containing 1% bovine serum albumin (BSA), 1% Tween 20, and 0.9% NaCl. The sample is then filtered through a material effective to remove materials which may interfere with the assay, as described in PCT Pubn. No. 94/03814 (Cerelli). Suitable filter media include nitrocellulose-based materials, hydrophobic/high protein-binding materials, and charged hydrophilic materials. The filter is preferably incorporated into sample reservoir 18 and/or wick 24.

The soluble ligand is a Dpd- or Pyd-specific antibody, whose preparation is described in Cerelli. The antibody is labeled by conjugating to colloidal gold, or another colored particle. Such conjugates may be obtained from commercial sources or prepared by the method of Leuvering, as noted above. When a colloidal gold-antibody conjugate is used, it is generally applied to the reaction strip material in the presence of several weight percent of a stabilizing reagent such as sucrose, trehalose, or BSA, and/or 0.1 to 1 weight percent of a detergent such as Tween 20.

An analog of the analyte, also effective to bind to the antibody, is immobilized within the detection zone. A suitable analog is a pyridinoline (Pyd) or deoxypyridinoline (Dpd) compound which is effective to bind to the free analyte-specific antibody. Dpd, Pyd and derivatives can be isolated by fractionation of urine, using protocols described, for example, in Black, Siebel, and Cerelli.

The analog molecule is preferably applied to the support via a streptavidin-porcine serum albumin (PSA)-biotin complex, following a procedure such as that described in Cerelli. In a typical procedure, Dpd or Pyd bound to streptavidin is mixed with a PSA-biotin complex, and the mixture is applied to nitrocellulose with an inkjet sprayer. The reagents may be applied in a reverse gradient for more uniform product development, as described above. The coated nitrocellulose is then dried at 50° C. to bind the components.

The control position of the immunoassay cassette is used to determine the level of creatinine, as noted above, in the sample, by transferring an aliquot of sample to control zone 38. One method for determination of creatinine employs analyte-specific oxidase reagents. Creatinine amidohydrolase converts creatinine to creatine, which is converted by creatine amidinohydrolase to urea and sarcosine. Sarcosine oxidase, in turn, converts sarcosine to glycine and formaldehyde, with production of $H_2O_2$ (Hewett). The evolved $H_2O_2$, whose level corresponds to the level of creatinine in the sample, reacts with a donor molecule, in the presence of a peroxidase, to form a detectable colored dye. Urine creatinine concentration can also be determined by other known methods, such as those based on reaction with alkaline picrate (Cook).

The assay is carried out in the competitive-binding format described above. A typical operating sequence, where the cassette is incorporated into a cassette reader, is as follows. In this procedure, the control reaction is initiated as the assay is carried out (Phase 3), rather than subsequently.

Phase 1

Sample well and wash reservoir are loaded.

Reaction strip and control zone are separated from sample transfer strip (at-rest position).

Sample transfer strip is placed in contact with sample wick/filter; sample is loaded.

Phase 2

Cassette withdraws into reader.

Optical scan for dry membrane reflectance is made at detection zone.

Contact is established between reaction strip and sample transfer strip (first operational position).

Reaction strip fills with sample; volume is controlled by reaction strip dimensions (duration about 3 minutes).

Phase 3

Connection between sample transfer strip and reaction strip is broken.

Contact is made between wash reservoir, reaction strip and wash takeup pad, compressing wash and takeup support blocks (second operational position).

Wash liquid flow is initiated from wash reservoir through reaction strip to wash takeup pad.

Contact is established between control zone and sample transfer strip (third operational position).

Sample is transferred from sample transfer strip to control zone to initiate creatinine end point reaction.

(After approx. 4 seconds:) Contact is broken between sample transfer strip and control zone.

Contact remains between wash reservoir, reaction strip and wash takeup pad.

Wash liquid continues to flow across reaction strip (duration about 4 minutes).

Optical readings are taken to establish test completion.

The level of labelled antibody is then detected at the detection zone. A convenient method of quantitating the level of a colored reaction product, such as a dye or colloidal gold conjugate, is by reflectance spectroscopy, according to techniques known in the art. Colloidal gold is detected at the 540 nm absorption peak. Percent reflectance is converted to level of analyte (Dpd or Pyd) by comparison to reflectance of standard samples.

While the invention has been described with reference to specific methods and embodiments, it will be appreciated that various modifications may be made without departing from the invention.

It is claimed:

1. An immunoassay cassette for use in detecting an analyte in a body-fluid sample, comprising
   (a) a base;
   (b) a reagent support;
   (c) means for mounting said support on said base for relative movement with respect thereto from an initial at-rest position, to first and second operational positions,
      said base having (i) a sample well for containing said sample, (ii) a sample-transfer strip for transferring sample in the sample well to a sample-transfer position, (iii) a wash reservoir for containing a wash solution, (iv) a wash-transfer strip for transferring wash solution in the wash reservoir to a wash-transfer position, and (v) a takeup pad for imbibing wash solution;
      said reagent support having (i) an analyte detection zone, and (ii) a reaction strip, comprising capillary means for transferring said body fluid sample from the sample-transfer position to the detection zone, when the reagent support is moved to its first operational position, and for transferring wash solution from the wash-transfer position to the detection zone, when the reagent support is moved to its second operational position,
      said takeup pad being effective to imbibe liquid from said detection zone when the reagent support is moved to its second operational position; and
   (d) reagent means for producing a detectable, analyte-dependent reaction product at said detection zone, said reagent means being disposed in a fluid pathway defined by said sample-transfer strip, reaction strip, and detection zone.

2. The cassette of claim 1, wherein said mounting means include compressible supports on the base effective to support opposite ends of the reagent support.

3. The cassette of claim 1, wherein said relative movement from said first to said second operational position is effective to break contact between said sample-transfer position and said reaction strip, and to establish contact between said wash-transfer position and said reaction strip.

4. The cassette of claim 1, wherein said simple-transfer strip has an overhang region containing said sample transfer position, which is adapted to contact the reaction strip in the first operational position, and to shift to a position of non-contact with said reaction strip in the second operational position.

5. The cassette of claim 1, wherein the reagent support further includes a control reaction zone, and said mounting means is effective for relative movement between said support and said base effective to assume a third operational position, wherein contact is established between said sample transfer strip and said control reaction zone.

6. The cassette of claim 1, wherein said reagent means comprises a labelled ligand effective to bind selectively with said analyte, and said reaction product is a detectable analyte-ligand complex formed by such binding.

7. The cassette of claim 1, wherein said reagent means comprises (i) a labelled ligand effective to bind selectively with said analyte and (ii) a substance effective to competitively bind with said labelled ligand, and said reaction product is a detectable substance-ligand complex formed by such competitive binding.

8. The cassette of claim 1, wherein said body fluid sample is a urine sample and said analyte is pyridinoline or deoxypyridinoline.

9. The cassette of claim 1, further comprising a strip of uniform polymeric mesh disposed between and adjoining the reaction strip and the detection zone.

10. The cassette of claim 1, wherein said reagent means is applied to the detection zone in a reverse concentration gradient, such that the concentration of said reagent means increases in a downstream direction across the detection zone.

11. An assay apparatus for detecting an analyte in a body fluid sample, comprising an immunoassay cassette, said cassette comprising
   (a) a base;
   (b) a reagent support;
   (c) means for mounting said support on said base for relative movement with respect thereto from an initial at-rest position, to first and second operational positions,
      said base having (i) a sample well for containing said sample, (ii) a sample-transfer strip for transferring sample in the sample well to a sample-transfer position, (iii) a wash reservoir for containing a wash solution, (iv) a wash-transfer strip for transferring wash in the wash reservoir to a wash-transfer position, and (v) a takeup pad for imbibing wash solution;
      said reagent support having (i) an analyte detection zone, and (ii) a reaction strip, comprising capillary means for transferring said body fluid sample from the sample-transfer position to the detection zone, when the reagent support is moved to its first operational position, and for transferring wash solution from the wash-transfer position to the detection zone, when the reagent support is moved to its second operational position,
      said takeup pad being effective to imbibe liquid from said detection zone when the reagent support is moved to its second operational position; and
   (d) reagent means for producing a detectable, analyte-dependent reaction product at said detection zone, said reagent means being disposed in a fluid pathway defined by said sample-transfer strip, reaction strip, and detection zone,
      wherein the reagent support (b) further includes a control reaction zone, and said mounting means is effective for relative movement between said support and said base effective to assume a third operational position, wherein contact is established between said sample transfer strip and said control reaction zone, and further comprising a cassette reader, said reader having an aperture for receiving said cassette therein, and means for moving said base relative to said reagent support from the at-rest position of the cassette, to the first, second, and third operational positions of the cassette, at predetermined times.

12. The assay apparatus of claim 11, further comprising detector means to detect an assay reaction product within the detection zone.

* * * * *